(12) United States Patent
DeFrees

(10) Patent No.: US 7,323,316 B2
(45) Date of Patent: Jan. 29, 2008

(54) GLYCOSYLTRANSFERASE INHIBITORS

(75) Inventor: Shawn DeFrees, North Wales, PA (US)

(73) Assignee: Abaron Biosciences, Inc., Del Mar, CA (US)

( * ) Notice: Subject to any disclaimer, the term of this patent is extended or adjusted under 35 U.S.C. 154(b) by 441 days.

(21) Appl. No.: 10/658,823

(22) Filed: Sep. 8, 2003

(65) Prior Publication Data

US 2004/0048325 A1 Mar. 11, 2004

Related U.S. Application Data

(62) Division of application No. 09/577,120, filed on May 23, 2000, now abandoned.

(60) Provisional application No. 60/136,150, filed on May 24, 1999.

(51) Int. Cl.
 *C12Q 1/48* (2006.01)
(52) U.S. Cl. ....................................................... 435/15
(58) Field of Classification Search ...................... None
 See application file for complete search history.

(56) References Cited

OTHER PUBLICATIONS

Rabina et al. Analytical Biochemistry 1997;246:71-78.*
Sousa et al. Cell Mol Biol 1996;42:609-616.*
Chung et al. Biooranic & Medicinal Chemistry Letters 1998;8:3359-3364.*
Sambandam et al. Archives of Biochem and Biophysics 1987;254(2):579-585.*
Inokuchi, J-I, et al., "Preparation of the active isomer of 1-phenyl-2-decanoylamino-3-morpholino-1-propanol, inhibitor of murine glucocerebroside synthetase," *Journal of Lipid Research*, 1987, pp. 565-571, vol. 28, Bethesda, MD, US.
Kato, S. et al., "Inhibition of lipid-linked oligosaccharide synthesis by aryl phosphates," *The Biochemical Journal*, Apr. 15, 1981, pp. 71-79, vol. 196, No. 1, The Biochemical Society, London.
Lee, L., et al., "Improved Inhibitors of Glucosylceramide Synthase," *The Journal of Biological Chemistry*, May 21, 1999, pp. 14662-14669, vol. 274, No. 21, American Society for Biochemistry and Molecular Biology, Inc., Baltimore, MD, US.
Mead, R., et al. "Inhibition of Purified Rabbit Muscle Phosphorylase *a* and Phosphorylase *b* by Polychlorinated Biphenyls, Polychlorinated Biphenylols and Polybrominated Biphenyls," *Biochimica et Biophysica Acta*, 1982, pp. 173-179, vol. 701, No. 2, Elsevier Biomedical Press.
Mitranic, M., et al., "The Effect of Linoleic Acid and Benzyl Alcohol on the Activity of Glycosyltransferases of Rat Liver Golgi Membranes and Some Soluable Glycosltransferases," *Biochimica et Biophysica Atca*, 1982, pp. 75-84, vol. 693, No. 1, Elsevier Biomedical Press.
Olshefski, R., et al, "Synthesis, Shedding, and Intercellular Transfer of Human Medulloblastoma Gangliosides: Abrogation by a New Inhibitor of Glucosylceramide Synthase," *Journal of Neurochemistry*, 1998, pp. 467-472, vol. 70, No. 2, Lippincott-Raven Publishers, Philadelphia, PA, US.
Scudder, P., et al., "Glycosyltransferases of the Human Cervical Epithelium I. Characterization of a β-Galactoside α-2-L-Fucosyltransferase and the Identification of a β-N-Acetylclucosaminide α-3-L-Fucosyltransferase," *Biochimica et Biophysica Acta*, 1981, pp. 128-135, vol. 660, No. 1, Elsevier/North-Holland Biomedical Press.
Shimizu, T., et al., "Partial Purification and Characterization of UDPG: *t*-Cinnamate Glucosyltransferase in the Root of Sweet Potato, *Ipomoea batatas* Lam," *J. Biochem*, 1984, pp. 205-212, vol. 95, No. 1.
Tudek, B., et al., "Activity of *Escherichia coli* DNA-glycosylases on DNA damaged by methylating and ethylating agents and influence of 3-substituted adenine derivatives,"*Mutation Research*, 1998, pp. 169-176, vol. 407, No. 2, Elsevier.
Vunnam, R., et al., "Anaglos of Ceramide That Inhibit Glucocerebroside Synthetase in Mouse Brain," *Chemistry and Physics of Lipids*, 1980, pp. 265-278, vol. 26, Elsevier/North-Holland scientific Publishers, Ltd.
Warren, K., et al., "Glycosyltransferases of Rat Brain that Make Cerebrosides: Substrate Specificity, Inhibitors, and Abnormal Products," *Journal of Neurochemistry*, 1976, pp. 1063-1072, vol. 26, Pergamon Press, UK.
Wiewig, G., et al., "Dependence of Starch Synthase Activity From Maize Leaves on Light, pH and Redox State," *Acta Physiologica Latino Americana*, 1976, pp. 415-423, vol. 26, No. 5.
Database Biosis Online!: Thaniyavarn, S., et al., "Pyridine Analogs Inhibit the Glucosyl Transferase EC-2.4.1.5 of Streptococcus-Mutans," *Infection and Immunity*, 1982, 1 page, Bioscience Information Service, Philadelphia, PA, US.
Ichikawa, Yoshitaka, et al. "Chemical-Enzymatic Synthesis and Conformational Analysis of Sialyl Lewis x and Derivatives", *J. Am. Chem. Soc.* (1992) 114:9283-9298.
Wong, Chi-Huey, et al. "Specificity, Inhibition and Synthetic Utility of a Recombinant Human α-1,3, Fucosyltransferase", *J. Am. Chem. Soc.* (1992) 114:7231-7322.
Qiao, Lei, et al. "Synergistic Inhibition of Human α-1,3, Fucosyltransferase V", *J. Am. Chem. Soc.* (1996) 118:7653-7662.
Chatterjee, Subroto, "Oxidized low density lipoproteins and lactosylceramide both stimulate the expression of proliferating cell nuclear antigen and the proliferation of aortic smooth muscle cells" *Indian Journal of Biochemistry & Biophysics*, (1997) 34:56-60.
Takayama, Suichi, et al. "Selective Inhibition of β-1,4- and α-1,3-Galactosyltransferases: Donor Sugar-Nucleotide Based Approach", *Bioorganic & Medicinal Chemistry* (1999) 7:401-409.
Broquet, Pierre, et al. "Effect of Desipramine on a Glycoprotein Sialyltransferase Activity in C6 Cultured Glioma Cells", *Journal of Neurochemistry*, (1990) 54(2):388-394.

* cited by examiner

*Primary Examiner*—Ralph Gitomer
*Assistant Examiner*—Bin Shen
(74) *Attorney, Agent, or Firm*—Townsend and Townsend and Crew LLP

(57) ABSTRACT

This invention provides potent inhibitors of glycosyltransferases. The glyscosyltransferase inhibitors are useful for inhibiting the synthesis of glycosides. Accordingly, the glycosyltransferase inhibitors find use, for example, in the modulation of biological processes that involve glycoside-mediated cell adhesion.

10 Claims, 18 Drawing Sheets

Rational Inhibitor Design

Inhibitor-Glycosyltransferase Binding Interactions

GLYCOSYLTRANSFERASE INHIBITORS

CROSS REFERENCE TO RELATED APPLICATIONS

This application claims priority to U.S. Ser. No. 60/136,150 filed May 24, 1999, which is incorporated herein by reference.

FIELD OF THE INVENTION

This invention pertains to the field of glycosyltransferase inhibitors. Compounds that inhibit glycosyltransferases, as well as methods for identifying them are provided. Also provided are methods of inhibiting glycosyltransferases and methods of modulating biological processes that involve glycosylation.

BACKGROUND OF THE INVENTION

Carbohydrates are ubiquitous throughout the plant and animal kingdoms. The structures are known to play a number of important roles in many biological processes. For example, carbohydrates are involved in intercellular recognition in mammalian cells. In fungi and plants, carbohydrates are an important structural component in cell walls. Carbohydrates are typically synthesized by enzymes such as glycosyltransferases, which are a group of enzymes that transfer a monosaccharide from an activated sugar nucleotide to acceptor oligosaccharides found on glycoproteins, glycolipids or polysaccharides. Because of the importance of glycosylation in biological systems, it is highly desirable to develop efficient inhibitors for glycosyltransferases and other enzymes involved in the metabolism of carbohydrates. While there has been increasing attention placed on development of glycosyltransferase inhibitors in recent years, there are as yet no glycosyltransferase inhibitors reported that match the characteristics desired for a therapeutic compound.

Most of the work done on glycosyltransferases to date has focused on hydrophilic analogs of the donor and acceptor substrates of these enzymes. (Hashimoto et al. *J Org Chem* 62:1914-1915 (1997); Hashimoto et al. *J Synth Org Ch Japan* 55, 325-333 (1997); Muller et al. *Angewandte Chemie-International Edition* 37: 2893-2897 (1998); Amann et al. *Chemistry-A European Journal* 4:1106-1115 (1998); Murray et al. *Biochemistry* 36, 823-831 (1997); Kim et al. *J Am Chem Soc* 121:5829-5830 (1999), Schmidt et al. *Bioorg Med Chem* 3, 1747-1750 (1993); Miura et al. *Bioorg Med Chem* 6, 1481-1489 (1998); and Palcic et al. *J Biol Chem* 264, 17174-17181 (1989)). The best inhibitors are generally in the μM range, but inhibitors of up to 14 nM have been obtained for a sialyltransferase(Muller et al., supra). Typically, the inhibitors are negatively charged, and therefore unlikely to be orally available unless a suitable prodrug form is identified.

Most inhibitors based on acceptor substrates are synthetic di- or trisaccharide acceptors that bind to the enzyme, but the hydroxyl group to which the transfer normally occurs has been removed (deoxy-) or substituted (e.g. amino group) Kajihara et al. *Carbohydr Res* 247:179-193 (1993); Stults et al. *Glycobiology* 9:661-668 (1999); Lu et al. *Bioorg Med Chem* 4, 2011-2022 (1996); Lowary et al. *Carbohydr Res* 251:33-67 (1994); Khan et al. *J Biol Chem* 268:2468-2473 (1993). In general the Ki values of the inhibitors are in the range of the Km value of the acceptor substrates that they replace. However Ki values on the order of 10 μM have been reported for an α-galactosyltransferase (Lowary et al., supra) and for N-acetylglucosaminyltransferase V (Khan et al., supra).

As a class, prior art oligosaccharide based inhibitors are not expected to cross cell membranes and would be considered poor candidates for a therapeutic. However, several groups have demonstrated that disaccharide acceptor substrates suitably modified with hydrophobic aglycons and/or acetyl esters readily enter cells, reach the Golgi compartment. Terminal glycosylation of cell surface glycoproteins can be thus be inhibited due to competitive glycosylation of the disaccharide substrates which are then secreted (Neville et al. *Biochem J*:307, 791-797 (1995); Kuan et al. *J Biol Chem* 264:19271-19277 (1989); Sarkar et al. *Proc Natl Acad Sci USA* 92:3323-3327 (1995); Sarkar et al. *J Biol Chem* 272:25608-25616 (1997)).

Other compounds such as N-butyldeoxynojirimycin (NB-DNJ) and N-butyldeoxygalactonojirimycin (NB-DGNJ) have been shown to be inhibitors of glucosylceramide synthetase. N-butyldeoxynojirimycin is better known as a glucosidase inhibitor, but was found to inhibit the enzyme that initiates the synthesis of glucosylceramides by attaching glucose to ceramide (Platt et al. *J Biol Chem* 269:8362-8365 (1994) and Platt et al. *J Biol Chem* 269:27108-27114 (1994). NB-DNJ has been demonstrated to reduce glycolipid synthesis in mice (Platt et al. *J Biol Chem* 272:19365-19372 (1997) Jeyakumar et al. *Proc Natl Acad Sci USA* 96:6388-6393 (1999); and Andersson et al. *Biochem Pharmacol* 59:821-829 (2000)).

Based on the above, it is clear that compounds that specifically modulate the activity of particular glycosyltransferases can be useful to control of number of biological processes. Therefore, a need exists for highly efficient inhibitors of glycosyltransferases. The present invention fulfills this and other needs.

SUMMARY OF THE INVENTION

The present invention provides inhibitors of glycosyltransferase activity that are preferably based on the hydrophobic interactions between the carbohydrate portion of the enzyme substrates, or product, and the glycosyltransferase. The inhibitors of the invention can be used to inhibit the activity of glycosyltransferases involved in the synthesis of carbohydrates associated with a number of biological processes. Methods are also disclosed for preparing the glycosyltransferase inhibitors as well as various screening assays to identify suitable candidates.

Therapeutic and other uses for these compounds are also provided. The inhibitors of the invention can be used, for example, to control glycosyltransferase activity in vitro. For example, the inhibitors can used to inhibit glycosyltransferase activity in cell cultures used to prepare desired carbohydrate structures. The inhibitors are also conveniently used to produce animal models of disease by selectively inhibiting desired glycosyltransferases in vivo. In addition, the methods of the invention can be used therapeutically, to modify carbohydrates associated with disease.

In particular, the invention provides methods for designing glycosyltransferase inhibitors. The methods comprise providing a non-carbohydrate test compound which interacts with hydrophobic moieties (e.g., amino acid residues) in the active site of the glycosyltransferase. The test compound is contacted with the glycosyltransferase under conditions suitable for the glycosyltransferase to transfer a monosaccharide from a donor substrate to an acceptor substrate. This is followed by quantitative detection of the glycosylated product to determine the degree to which the activity of the enzyme is decreased in the presence of the test compound.

Usually, the test compound comprises a ring structure that mimics the pyranose rings of the acceptor, donor substrate or product of the reaction. Typically, the ring is a planar ring structure. For example, the test compound may contain an aromatic ring, a heteroaromatic ring, or an aliphatic ring structure.

Any number of glycosyltransferases from either eukaryotic (e.g., mammals, insects, plants, or fungi) or prokaryotic (e.g. bacteria) organisms can be used in the assays. For example, fucosyltransferases (e.g., FTVII, FTIV, or FTIII), sialyltransferases (ST6Gal1 or ST3Gal1) and galactosyl transferases (e.g., α(1,3)Gal T) can be used. The glycosyltransferase can be present in the assay in a number of forms, depending upon the assay format. For example, the enzyme can be expressed in a transgenic cell or it can be expressed constitutively in a normal cell.

In the assays, the means by which the product is detected is not critical and will depend upon the assay format. For example, one of the enzyme substrates can be labeled (e.g., radioactive labels, fluorescent labels and the like) and labeled product is detected. Alternatively, the product can be detected by using an antibody that is specifically immunoreactive with the product. Preferred assay formats include high throughput assays based on an ELISA format, radioactive column assays, and cellular assays.

The test compounds used in the assays, as noted above, will typically be designed to interact with hydrophobic residues in the active site of the target glycosyltransferase. Compounds or analogs thereof having structures suitable for this purpose are preferably used. Ideally, the compounds will have an IC50 in the nanomolar range, when tested in the assays described herein. Thus, inhibitors will usually have an IC50 of less than about 100 μM, usually less than about 10 μM, and often less than about 100 nM.

Definitions

The term sugar as used herein refers to a carbohydrate compound, comprising one or more saccharide units usually an aldehyde or ketone derivative of a polyhydric alcohol, particularly of the pentahydric and hexahydric alcohols. For description of saccharide structure and nomenclature see, *Essentials of Glycobiology*, Varki et al. eds., Chapter 2 (Cold Spring Harbor Press, Cold Spring Harbor, N.Y., 1999). Exemplary sugars and their commonly used abbreviations are as follows:

Ara=arabinose;
Fru=fructose;
Fuc=fucose;
Gal=galactose;
GalNAc=N-acetylgalactosamine;
Glc=glucose;
GlcNAc=N-acetylglucosamine;
Man=mannose; and
NeuAc=N-acetylneuraminic acid
Sia=sialic acid Other examples of sugars include glucosamine, galactosamine, rhamnose, ribose, glucuronic acid, N-acetylmuramic acid, xylose. The term also encompasses various sugar derivatives such as deoxy derivatives, anhydrouronic acids, chloro derivatives, fluoro derivatives and amino sugars (e.g., N-butyldeoxynojirimycin).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose.

In the description of chemical compounds, terms are generally used according to their standard meanings. The term "alkyl" as used herein means a branched or unbranched, saturated or unsaturated, monovalent or divalent, hydrocarbon radical having from 1 to 20 carbons, including lower alkyls of 1-8 carbons such as methyl, ethyl, n-propyl, butyl, n-hexyl, and the like, cycloalkyls (3-7 carbons), cycloalkylmethyls (4-8 carbons), and arylalkyls.

The term "alkoxy" refers to alkyl radicals attached to the remainder of the molecule by an oxygen, e.g., ethoxy, methoxy, or n-propoxy.

The term "acyl" refers to a radical derived from an organic acid by the removal of the hydroxyl group. Examples include acetyl, propionyl, oleoyl, myristoyl.

The term "aryl" refers to an aromatic monovalent carbocyclic radical having a single ring (e.g., phenyl) or multiple condensed rings (e.g., naphthyl), which can optionally be mono-, di-, or tri-substituted, independently, with alkyl, lower-alkyl, cycloalkyl, hydroxylower-alkyl, amino lower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. Alternatively, two adjacent positions of the aromatic ring may be substituted with a methylenedioxy or ethylenedioxy group.

The term "heteroaryl," as used herein, refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl." Compounds or analogs thereof having structures suitable for this purpose are conveniently used.

Examples of suitable classes of compounds that have heteroaryl ring structures include, but are not limited to, quinolines, arylsulfonamides, phenothiazines, carbazoles, benzamides and benzopyranones.

1A. shows the interaction between a monosaccharide and the active site of a glycosyltransferase;

1B. shows the interaction between an oligosaccharide and the active site of a glycosyltransferase;

1C. shows a disaccharide bound to a glycosyltransferase;

1D shows the inhibitor design concept of the invention;

1E shows inhibitor-glycosyltransferase interactions.

Figure 2:
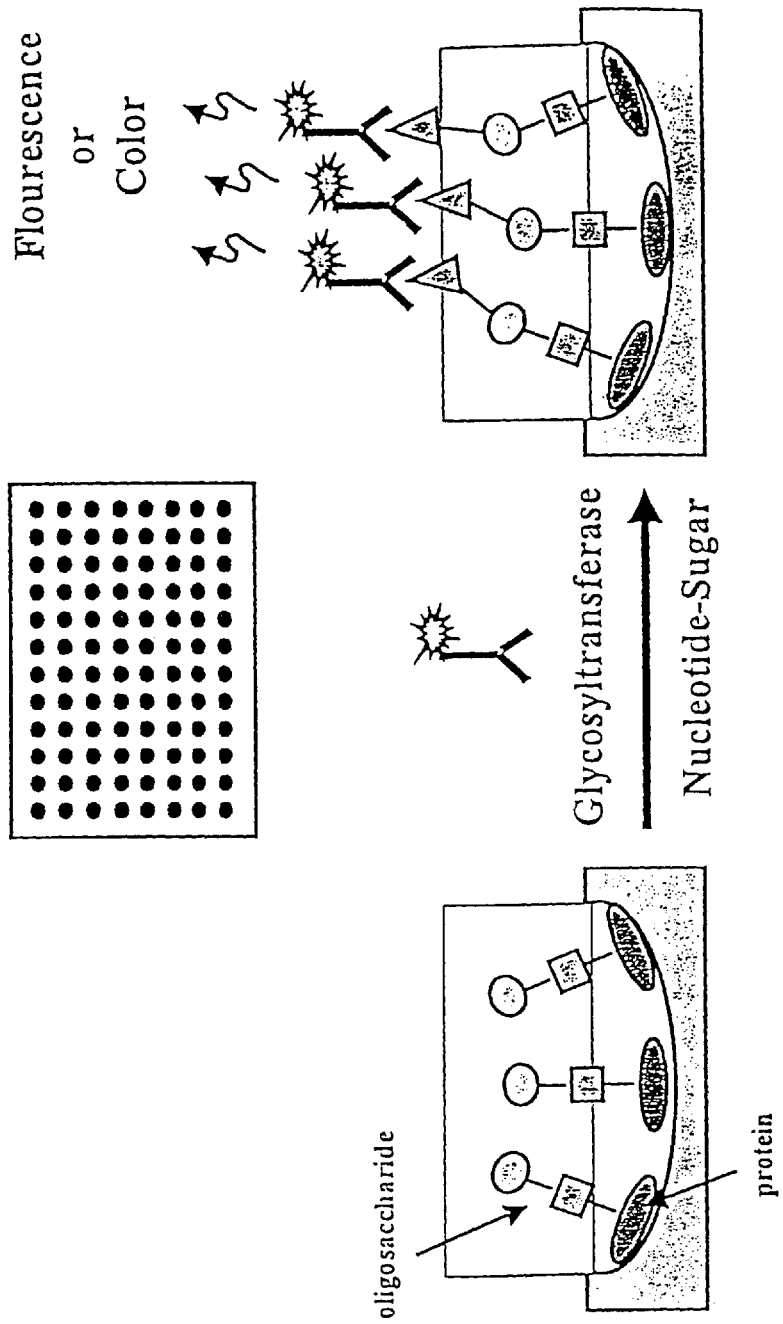

FIG. 2 shows the steps in an ELISA format assay of the invention.

Figure 3:
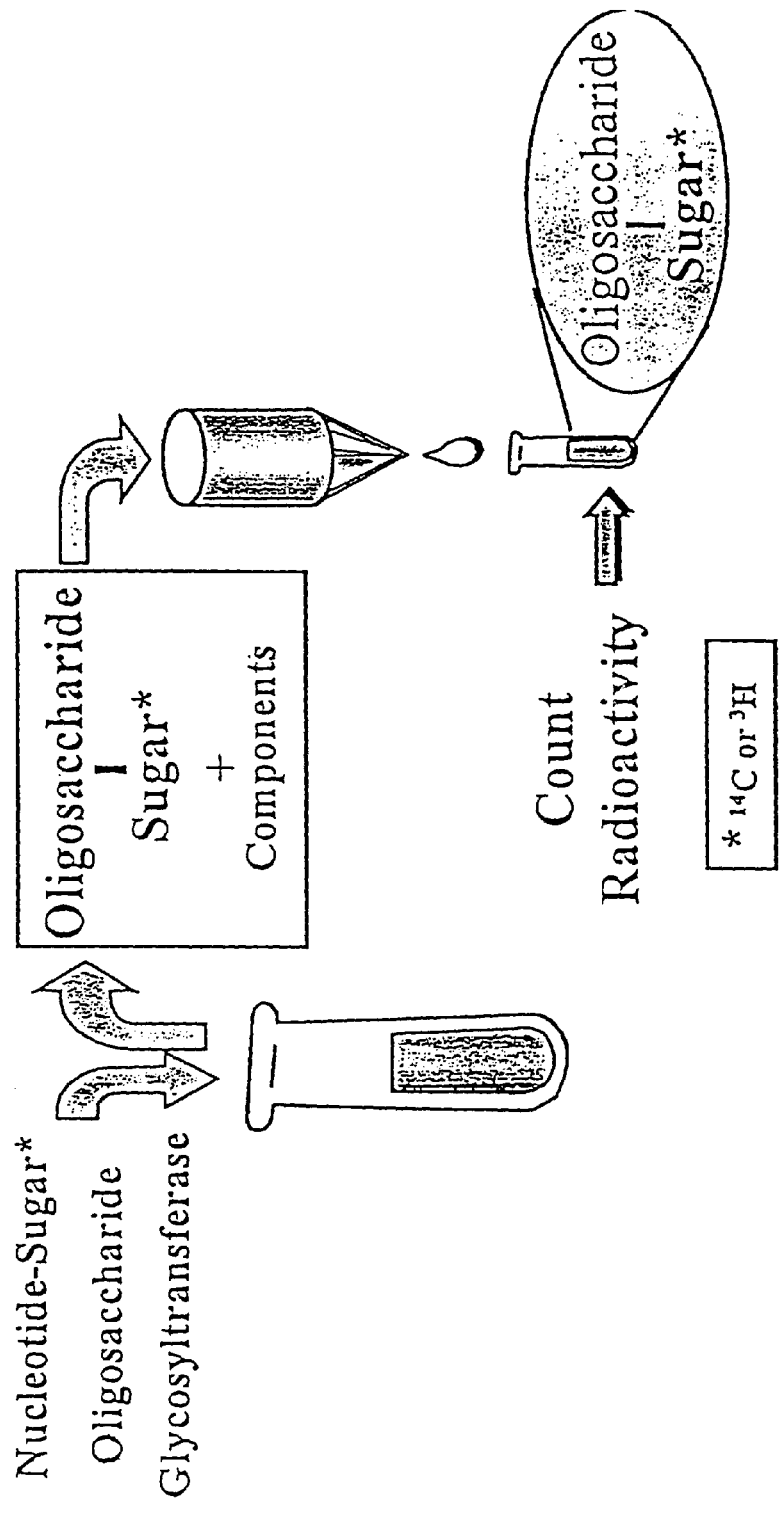

FIG. 3 shows the steps in a radioactive column assay of the invention.

Figure 4:
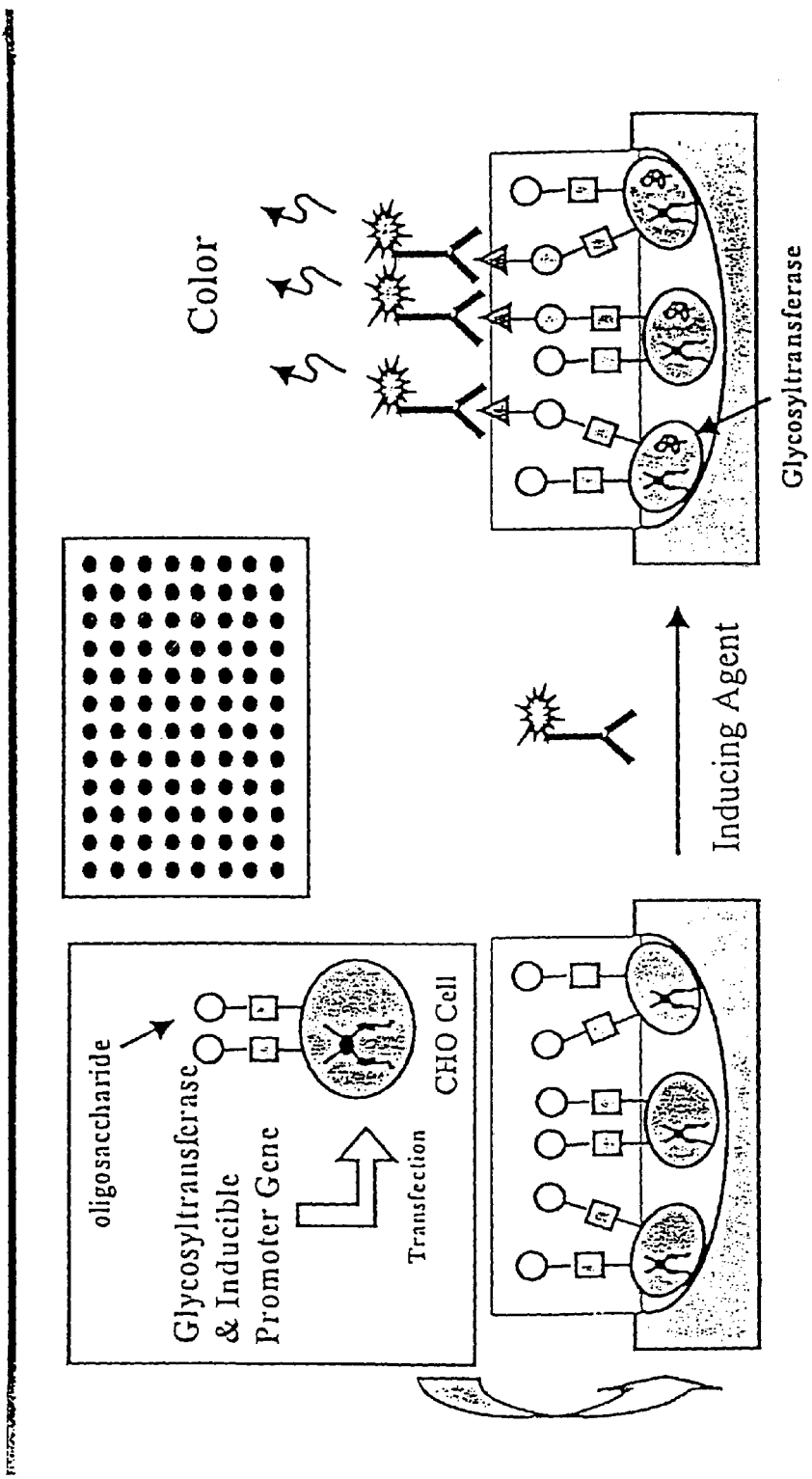

FIG. 4 shows the steps in a cell-based assay of the invention.

Figure 5:
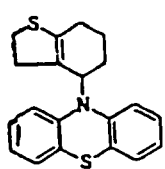
Figure 5:
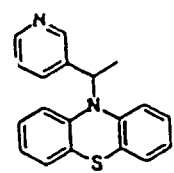
Figure 5:
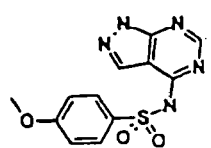
Figure 5:
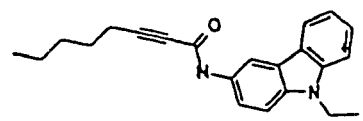
Figure 5:
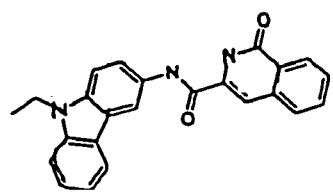
Figure 5:
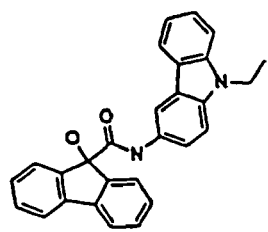
Figure 5:
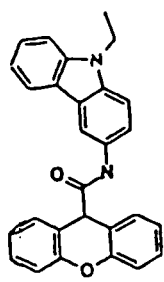
Figure 5:
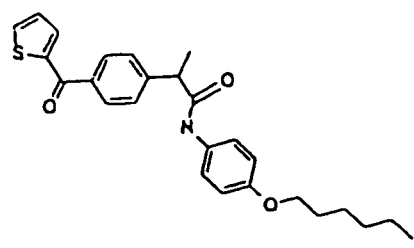
Figure 5:
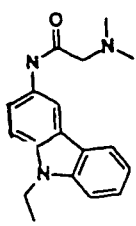
Figure 5:
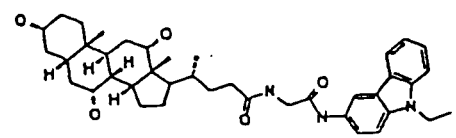
Figure 5:
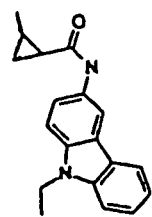
Figure 5:
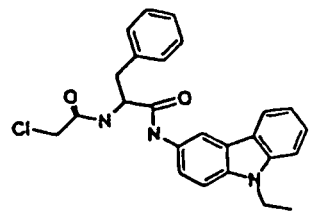
Figure 5:
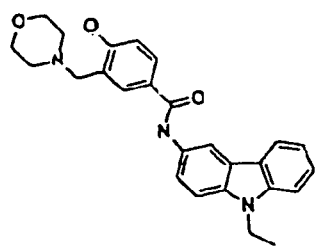
Figure 5:
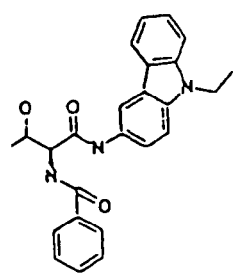
Figure 5:
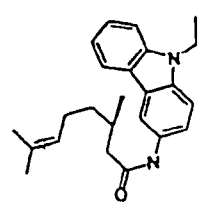
Figure 5:
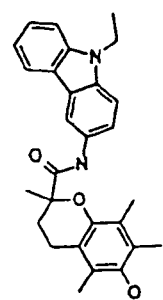
Figure 5:
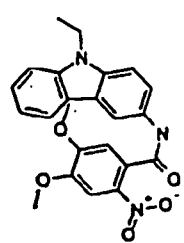
Figure 5:
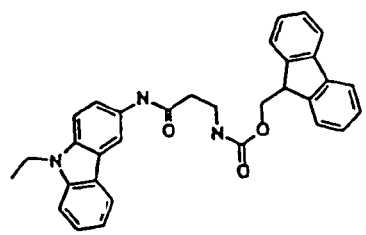
Figure 5:
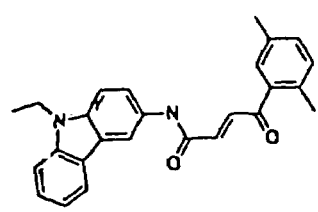
Figure 5:
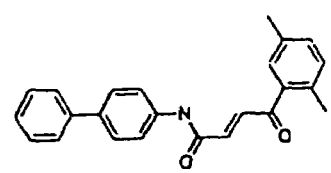
Figure 5:
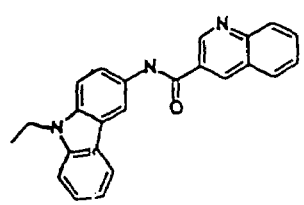
Figure 5:
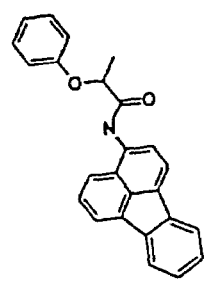
Figure 5:
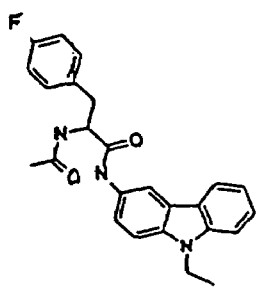
Figure 5:
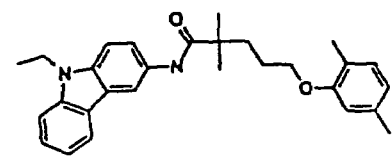
Figure 5:
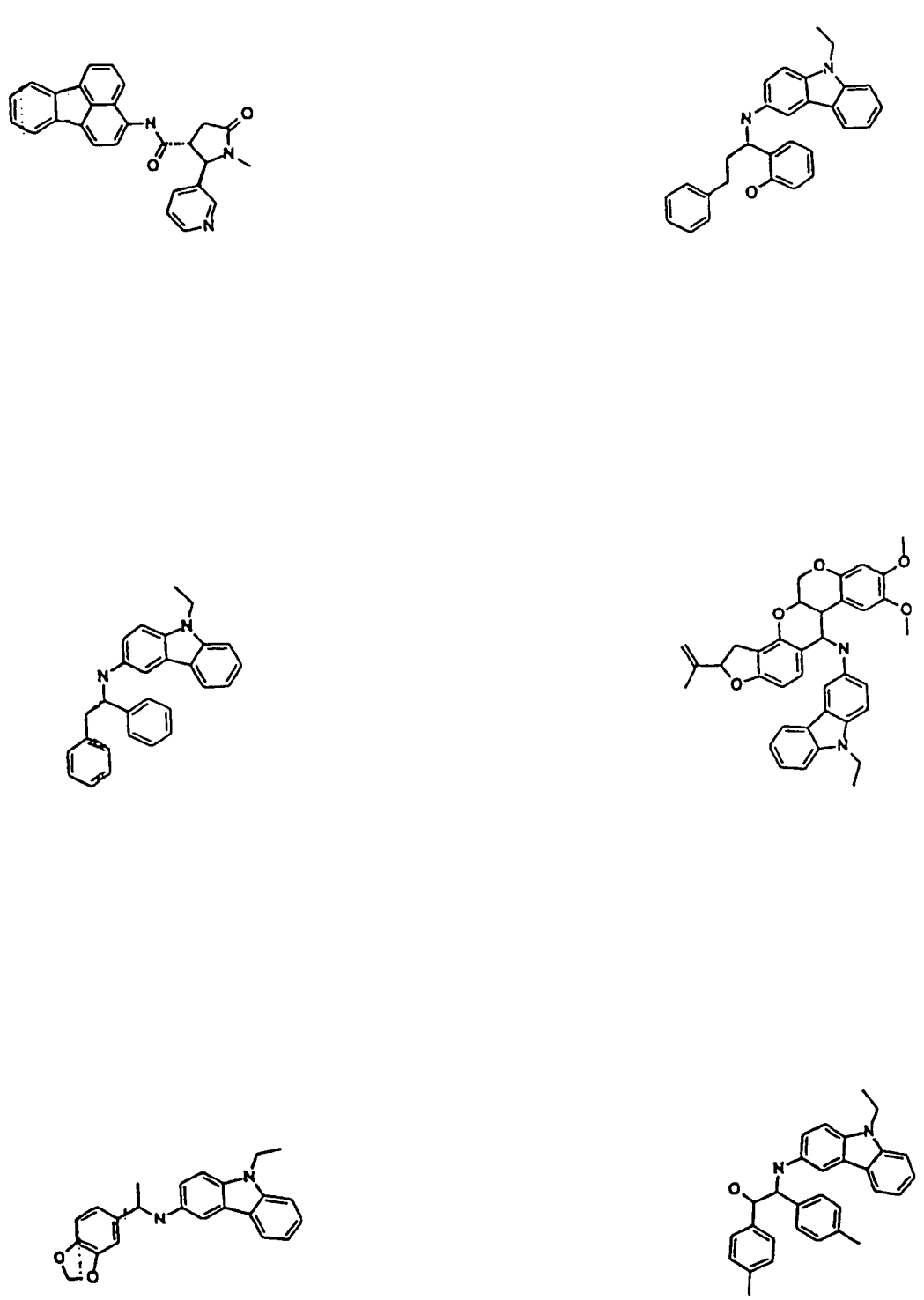
Figure 5:
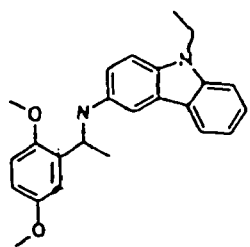
Figure 5:
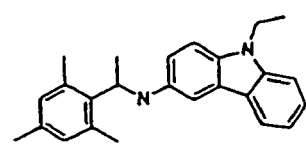
Figure 5:
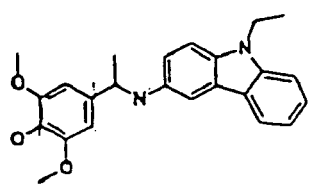
Figure 5:
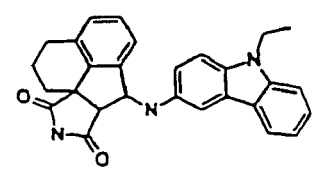
Figure 5:
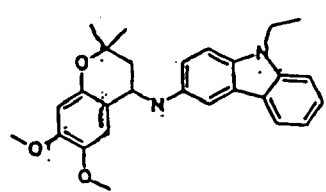
Figure 5:
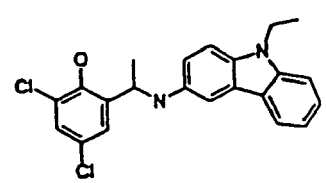
Figure 5:
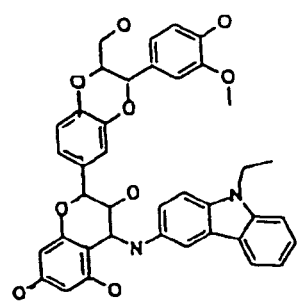
Figure 5:
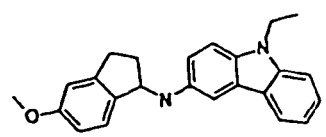
Figure 5:
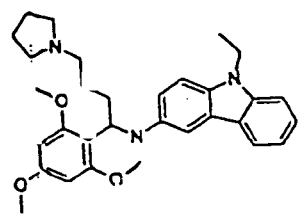
Figure 5:
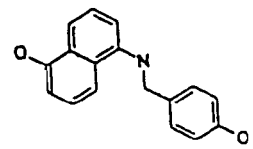
Figure 5:
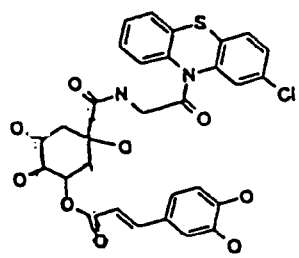
Figure 5:
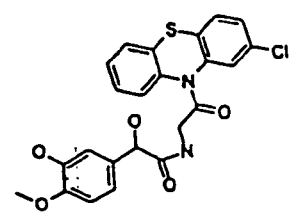
Figure 5:
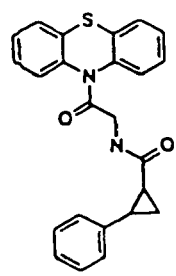
Figure 5:
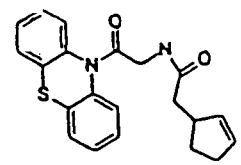
Figure 5:
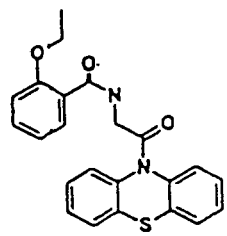
Figure 5:
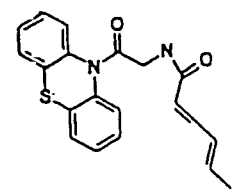
Figure 5:
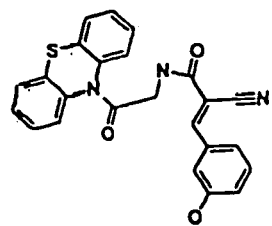
Figure 5:
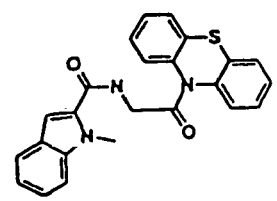
Figure 5:
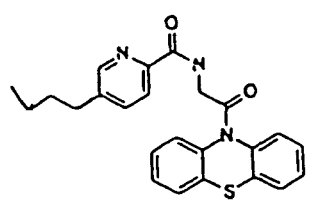
Figure 5:
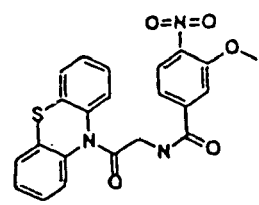
Figure 5:
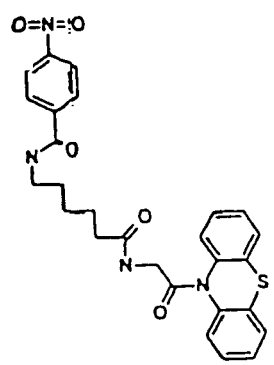
Figure 5:
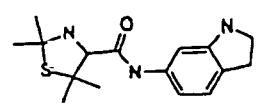

FIG. 5 shows structures of exemplary inhibitors of the invention.

Figure 6:
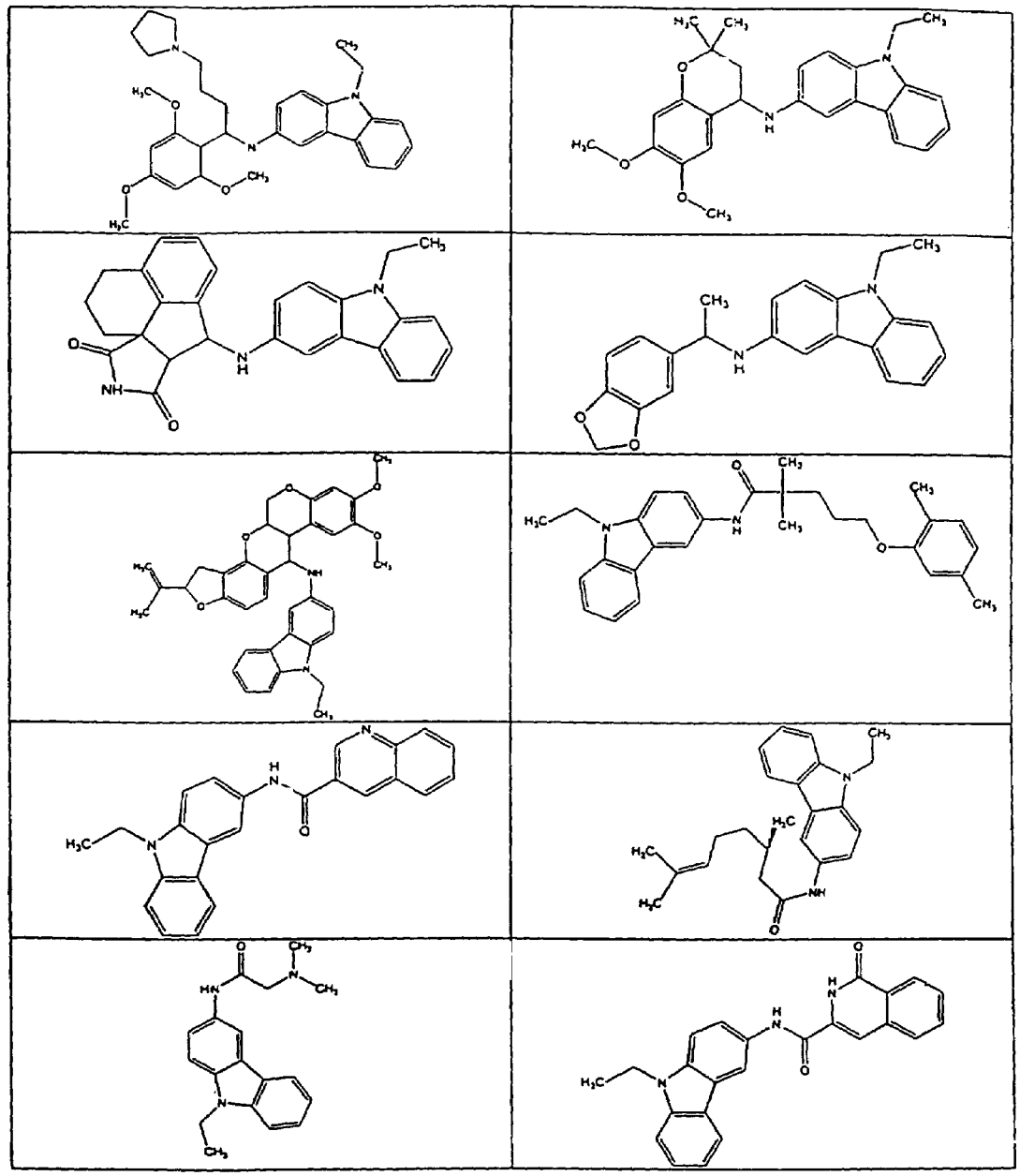

FIG. 6 shows structures of presently preferred inhibitors of the invention.

DETAILED DESCRIPTION

The present invention provides methods for the identification of glycosyltransferase inhibitors. Glycosyltransferases catalyze the transfer of a monosaccharide from a sugar nucleotide, the donor substrate, to an acceptor substrate. The acceptor substrate can be essentially any other group capable of accepting a glycosyl residue including, but not limited to, glycosyl residues, polypeptides, and lipids. The choice of appropriate substrate is typically dependent on the specificity of the transferase. See, generally, Beyer et al., *Adv. in Enzym.* 52:24 (1981).

The structures of presently known glycosyltransferase inhibitors are primarily based on hydrophilic structural motifs found in the donor substrate (i.e., arrangements of hydroxyl groups). In contrast, the inhibitors of the present invention are based on hydrophobic structural motifs found in the carbohydrate portion of acceptor or donor substrates for the enzymes and also in the products of the enzymatic reaction (see, e.g., Boume et al. *Current Opinion in Structural Biology* 3, 681-686 (1993) and Gabius et al. *Pharm Res* 15, 23-30 (1998)). Thus, the inhibitors and assay methods of the invention take advantage of the hydrophobic interactions involved in the recognition of the acceptor substrate by the glycosyltransferase. As a consequence, the inhibitors of the invention preferably have hydrophobic prioperties and are non-carbohydrate compounds that interact with hydrophobic amino acids in the active site of the target enzyme and compete with either the acceptor or donor substrate or the product. Without wishing to be bound by theory it is believed that hydrophobic residues in the active site contribute significantly to recognition of the natural acceptor substrate or product of the enzymatic reaction. In particular, bulky aromatic residues (e.g. Tyr, Trp, and Phe) or aliphatic residues (e.g. Leu, Ile, and Val) interact with the hydrophobic face of the sugars in the acceptor substrate or product (see, FIG. 1).

Figure 1A:
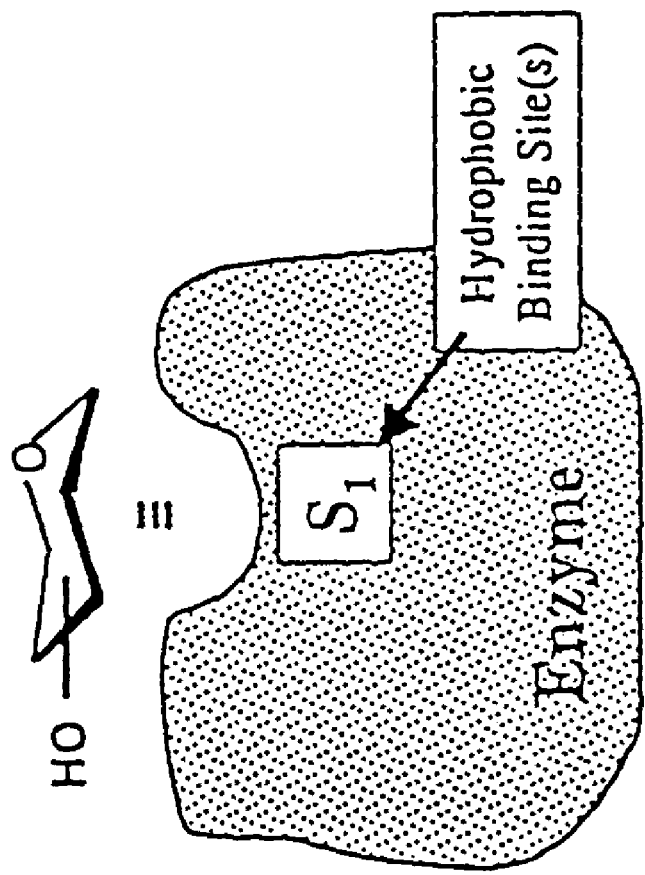
FIG. 1 shows the interaction of the hydrophobic face of an acceptor substrate with hydrophobic residues in the active site of a glycosyltransferase.
Figure 1B:
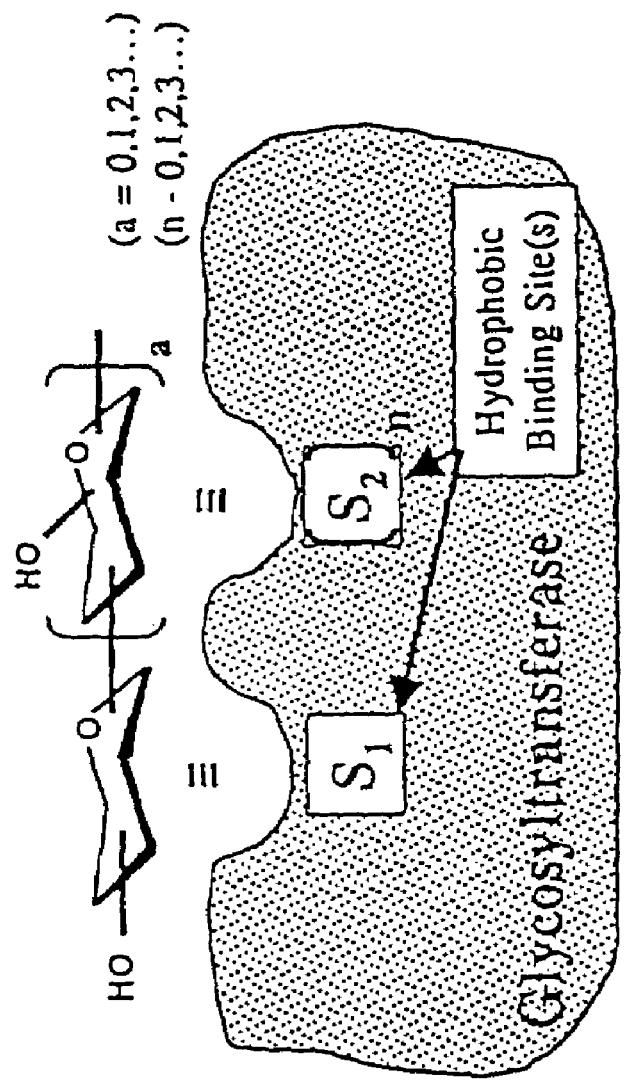
Figure 1C:
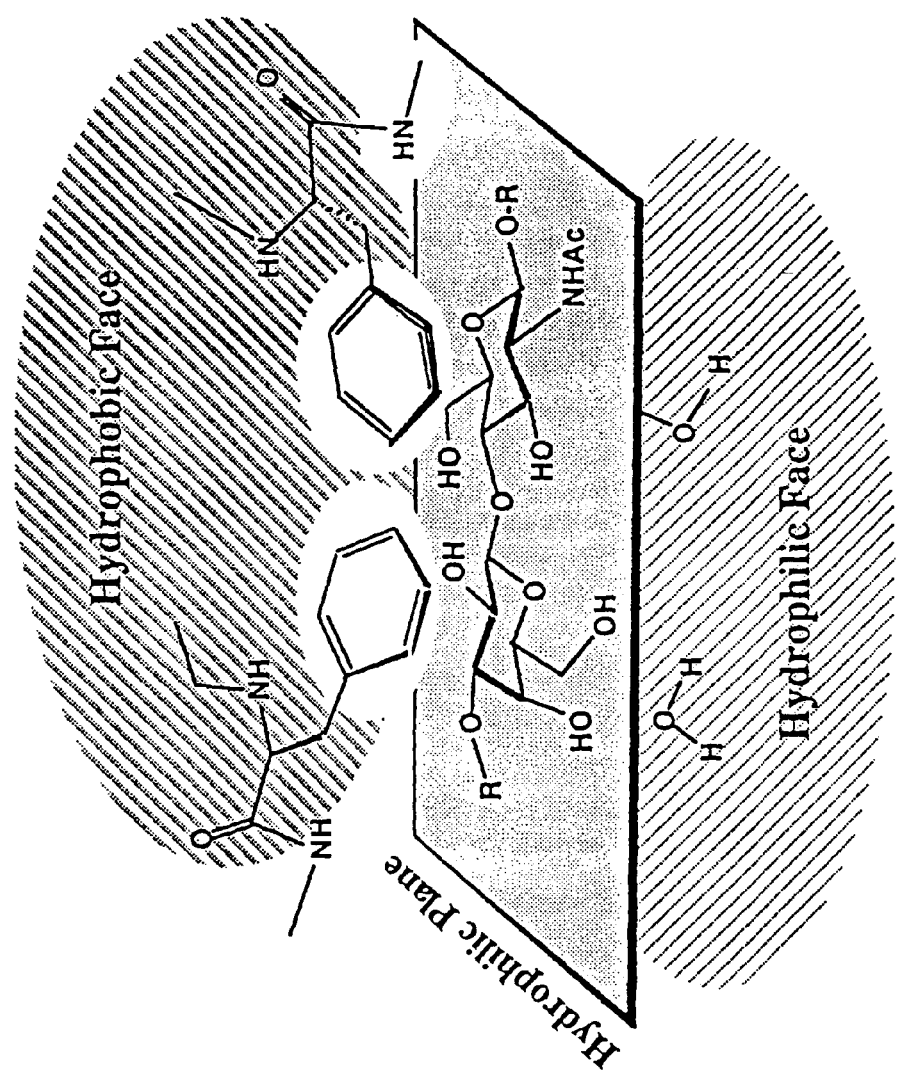
Figure 1D:
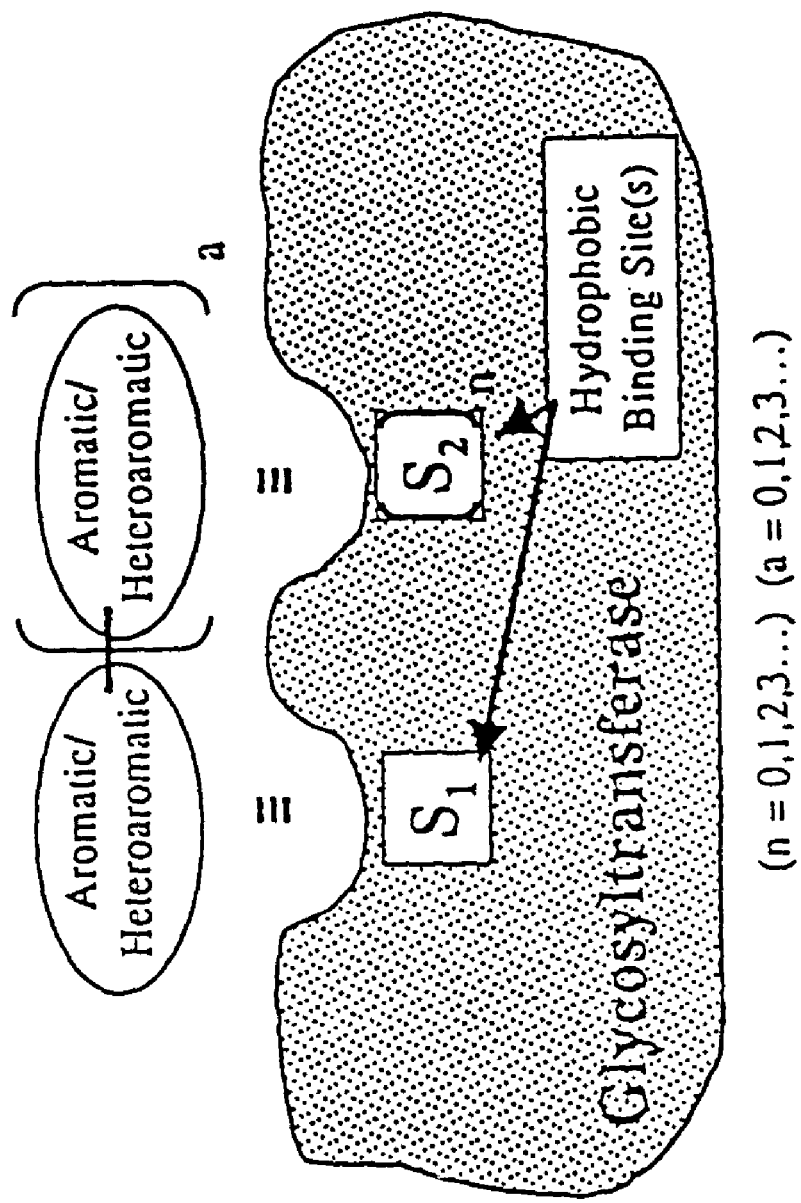
Figure 1E:
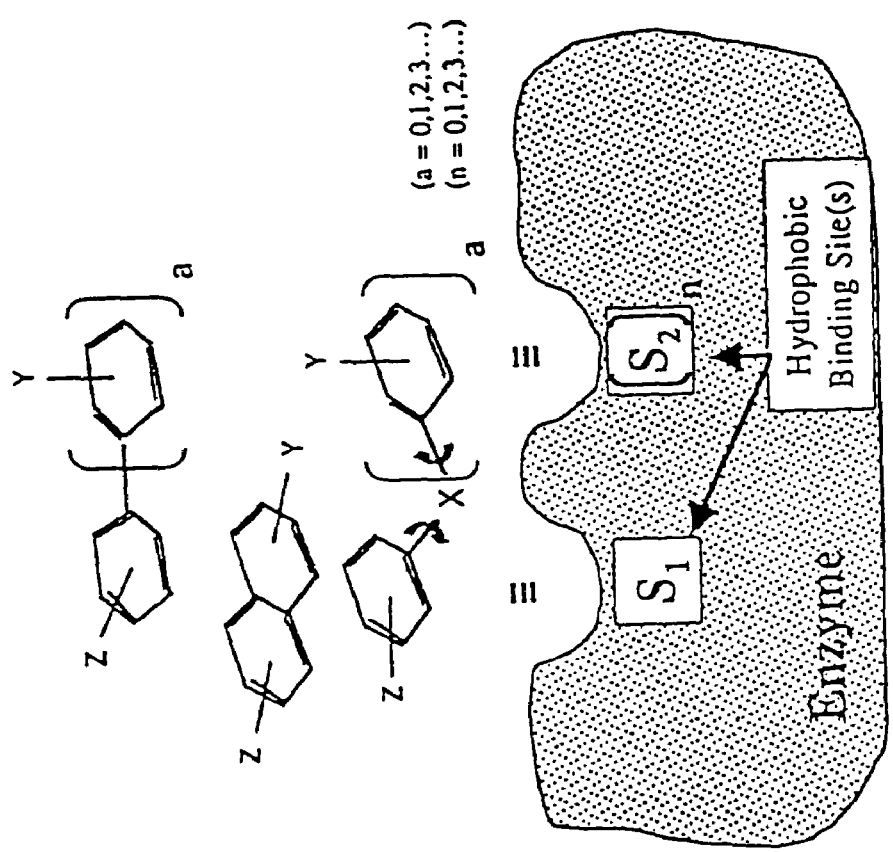

The inhibitors of the invention are based at least in part on the recognition that sugars interact with the glycosyltransferase active site through hydrophobic interactions (see, e.g., FIG. 1C). As shown in FIG. 1C, based on the orientation of the hydroxyl groups, sugars typically have a hydrophobic structural motif that interacts with hydrophobic amino acid residues in the protein. The inhibitors of the invention mimic the hydrophobic interaction or structure of the sugar substrates.

The non-carbohydrate inhibitors of the present invention are thus selected by their ability to mimic those portions of the acceptor or donor substrate and/or enzymatic product that interact with the hydrophobic residues in the active site. Using the disclosure provided herein, one of skill can design and test a wide variety of potential glycosyltransferase inhibitors. Typically, the inhibitors are selected for their ability to mimic the structure and arrangement of the pyranose rings of one or more of the sugars in the donor or acceptor substrate. For example, if the acceptor substrate contains more than one sugar, the inhibitor can be designed to mimic the spatial orientation between the sugars in the substrate or the product.

Since the inhibitors of the invention are based on hydrophobic interactions with the enzyme, design of the inhibitors can be facilitated by prediction of the relative hydrophobicity of candidate compounds. Means for determining the hydrophobicity of compounds are well known. Typically, hydrophobicity is expressed in terms of the Hansch constant. The Hansch constant is a measure of the capability of a solute for hydrophobic interaction based on the partition coefficient P for distribution of the solute between octanol and water. The most general way of applying P is as log P.

Selectivity and/or increased affinity of the inhibitors for particular glycosyltransferases can be achieved by adding substituents to a core structure that affect the hydrophobicity of the test compound. The behavior of various substituents may be quantified by a substituent constant, $\pi$. There are various $\pi$ scales, depending on the core structure used as reference. Tables providing $\pi$ constants for substituents are available (see, e.g., Hansch and Leo, (1979), "Substituent Constants for Correlation Analysis in Chemistry and Biology", Wiley, New York, Hansch et al. *J. Med. Chem.* 20:304 (1977), Hansch et al. *J. Med. Chem.* 16:1207(1973),). Using this information, the relative hydrophobicity of different substitutions can be ascertained and used to design inhibitors of the invention.

Inhibitors of the invention typically comprise one or more hydrophobic groups. Usually, the compounds will comprise aromatic, heteroaromatic, multiple ring aromatic or aliphatic ring structures or any hydrophobic group that interacts with the hydrophobic residues in the active site. Based on the hydrophobic interactions described above and substituent constants described above, one of skill can identify or synthesize a number of test compounds that meet these criteria. To identify inhibitors, the test compounds can be conveniently screened in standard assays to determine their ability to inhibit the activity of the selected enzyme.

One of skill will recognize that the inhibitors may be further modified to include various hydrophilic or charged groups to optimize potency. These moieties may be used, for example, to optimize avidity, solubility, bioavailablity or other aspects of the pharmacodynamics of the compounds.

The inhibitors of the invention can be used to inhibit the activity of enzymes from any organism involved in synthesis of carbohydrates. For example, suitable fungal, bacterial, insect and plant enzymes include chitin synthase, sucrose synthase, invertase, and other enzymes involved in carbohydrate metabolism and biosynthesis. Representative biosynthetic pathways include cell wall biosynthesis, polysaccharide biosynthesis and lipopolysaccharide biosynthesis (see, for example, Alberts et al., eds. Molecular Biology of the Cell, $2^{nd}$ Ed., Garland Publishing, Inc., London 1989; Dey et al., eds. Plant Biochemistry, Academic Press, San Diego 1997).

In mammals and other organisms, glycosyltransferases are grouped into families based on the type of sugar residue transferred. For example, enzymes that transfer sialic acid are called sialytransferases, those that transfer fucose are called fucosyltransferases, and those that transfer galactose are called galactosyltransferases. In each family there are typically 10-15 different enzymes required to elaborate the diverse carbohydrate structures found on glycoproteins and glycolipids of animal cells. Each enzyme makes a defined structure based on the donor and acceptor substrates they utilize, and the anomeric linkage formed in the transfer reaction.

A number of fucosyltransferases are known to those of skill in the art. Briefly, fucosyltransferases include any of those enzymes which transfer L-fucose from GDP-fucose to a hydroxy position of an acceptor sugar. In some embodiments, for example, the acceptor sugar is a GlcNAc in a Galβ(1→3,4)GlcNAc group in an oligosaccharide glycoside. Suitable fucosyltransferases for this reaction include the known Galβ(1→3,4)GlcNAc α(1→3,4)fucosyltransferase (FucT-III E.C. No. 2.4.1.65) which is obtained from human milk (see, e.g., Palcic et al., *Carbohydrate Res.* 190:1-11 (1989); Prieels, et al., *J. Biol. Chem.* 256:10456-10463 (1981); and Nunez, et al., *Can. J. Chem.* 59:2086-2095 (1981)) and the βGal(1→4)βGlcNAc α(1→3)fucosyltransferases (FucT-IV, FucT-V, FucT-VI, and FucT-VII, E.C. No. 2.4.1.65) which are found in human serum. A recombinant form of βGal(1→3,4)βGlcNAc α(1→3,4)fucosyltransferase is also available (see, Dumas, et al., *Bioorg. Med. Letters* 1:425-428 (1991) and Kukowska-Latallo, et al., *Genes and Development* 4:1288-1303 (1990)). Other exemplary fucosyltransferases include α1,2 fucosyltransferase (E.C. No. 2.4.1.69). An α1,3 fucosyltransferase IX (nucleotide sequences of human and mouse FucT-IX are described in Kaneko et al. (1999) *FEBS Lett.* 452: 237-242, and the chromosomal location of the human gene is described in Kaneko et al. (1999) *Cytogenet. Cell Genet.* 86: 329-330). Recently reported α1,3-fucosyltransferases that use an N-linked GlcNAc as an acceptor from the snail *Lymnaea stagnalis* and from mung bean are described in van Tetering et al. (1999) *FEBS Lett.* 461: 311-314 and Leiter et al. (1999) *J. Biol. Chem.* 274: 21830-21839, respectively. In addition, bacterial fucosyltransferases such as the α(1,3/4) fucosyltransferase of Helicobacter pylori as described in Rasko et al. (2000) *J Biol Chem* 275:4988-94; as well as the α1,2-fucosyltransferase of *H. Pylori* (Wang et al. (1999) *Microbiology*. 145:3245-53. See, also Staudacher, E. (1996) *Trends in Glycoscience and Glycotechnology*, 8: 391-408 for description of fucosyltransferases useful in the invention.

Exemplary galactosyltransferases include α1,3-galactosyltransferases (E.C. No. 2.4.1.151, see, e.g., Dabkowski et al., *Transplant Proc.* 25:2921 (1993) and Yamamoto et al. *Nature* 345:229-233 (1990), bovine (GenBank j04989), Joziasse et al. *J. Biol. Chem.* 264:14290-14297 (1989), murine (GenBank m26925), Larsen et al. *Proc. Nat'l. Acad. Sci. USA* 86:8227-8231 (1989), porcine (GenBank L36152), Strahan et al. *Immunogenetics* 41:101-105 (1995)). Another α1,3-galactosyltransferase is involved in synthesis of the blood group B antigen (EC 2.4.1.37), Yamamoto et al. *J. Biol. Chem.* 265:1146-1151 (1990), (human). Others include α1,4-galactosyltransferases, which include, for example, EC 2.4.1.90 (LacNAc synthetase) and EC 2.4.1.22 (lactose synthetase) (bovine (D'Agostaro et al. *Eur. J. Biochem.* 183:211-217 (1989)), human (Masri et al. *Biochem. Biophys. Res. Commun.* 157:657-663 (1988)), murine (Nakazawa et al. *J. Biochem.* 104:165-168 (1988)), as well as E.C. 2.4.1.38 and the ceramide galactosyltransferase (EC 2.4.1.45, Stahl et al. *J. Neurosci. Res.* 38:234-242 (1994)). Other suitable galactosyltransferases include, for example, α1,2-galactosyltransferases (from e.g., *Schizosaccharomyces pombe*, Chapell et al *Mol. Biol. Cell* 5:519-528 (1994)).

Mammalian serine/threonine-linked oligosaccharides (O-glycans) are commonly synthesized with the Golgi enzyme core 2 beta-1,6-N-acetylglucosaminyltransferase (C2 GlcNAcT). Core 2 O-glycans have been hypothesized to be essential for mucin production and selectin ligand biosynthesis. Mice lacking C2 GlcNAcT exhibit a restricted phenotype with neutrophilia and a partial deficiency of selectin ligands. Studies indicate that core 2 oligosaccharide biosynthesis segregates the physiologic roles of selectins and reveal a function for the C2 GlcNAcT in myeloid homeostasis and inflammation. Ellies et al. *Immunity* 9:881-90 (1998) WO99/27465).

Sialyltransferases include ST3Gal III, ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al. *Glycobiology* 6: v-xiv (1996)). An exemplary α2,3-sialyltransferase (EC 2.4.99.6) transfers sialic acid to the non-reducing terminal Gal of a Galβ1→4GlcNAc disaccharide or glycoside. See, Van den Eijnden et al., *J. Biol. Chem.*, 256:3159 (1981), Weinstein et al., *J. Biol. Chem.*, 257:13845 (1982) and Wen et al., *J. Biol. Chem.*, 267:21011 (1992). Another exemplary α2,3-sialyltransferase (EC 2.4.99.4) transfers sialic acid to the non-reducing terminal Gal of a Galβ1→3GalNAc disaccharide or glycoside. See, Rearick et al., *J. Biol. Chem.*, 254: 4444 (1979) and Gillespie et al., *J. Biol. Chem.*, 267:21004 (1992). Further exemplary enzymes include Gal-β-1,4-GlcNAc α-2,6 sialyltransferase (See, Kurosawa et al. *Eur. J. Biochem.* 219: 375-381 (1994)).

Some immune responses are mediated in part by 2,6-sialylgalactosides and 2,3-sialylgalactosides. These sialylgalactosides are ligands for cell surface molecules involved in intercellular adhesion and signal transduction, such as, for example, CD22. The 2,6-sialylgalactosides are typically involved in modulating immune responses mediated by B cells, while the 2,3-sialylgalactosides are generally involved in T cell mediated immune responses (see, e.g., WO98/54365).

Other glycosyltransferases include, for instance, glucosyltransferases, e.g., Alg8 (Stagljov et al., *Proc. Natl. Acad. Sci. USA* 91:5977 (1994)) or Alg5 (Heesen et al. *Eur. J. Biochem.* 224:71 (1994)), N-acetylgalactosaminyltransferases such as, for example, β(1,3)-N-acetylgalactosaminyltransferase, β(1,4)-N-acetylgalactosaminyltransferases (U.S. Pat. No. 5,691,180; Nagata et al. *J. Biol. Chem.* 267:12082-12089 (1992), and Smith et al. *J. Biol Chem.* 269:15162 (1994)) and polypeptide N-acetylgalactosaminyltransferase (Homa et al. *J. Biol Chem.* 268:12609 (1993)). Suitable N-acetylglucosaminyltransferases include GnTI (2.4.1.101, Hull et al., *BBRC* 176:608 (1991)), GnTII, and GnTIII (Ihara et al. *J. Biochem.* 113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase.

Also of interest are enzymes involved in proteoglycan synthesis, such as, for example, N-acetylgalactosaminyltransferase I (EC 2.4.1.174), and enzymes involved in chondroitin sulfate synthesis, such as N-acetylgalactosaminyltransferase II (EC 2.4.1.175). Suitable mannosyltransferases include α(1,2) mannosyltransferase, α(1,3) mannosyltransferase, β(1,4) mannosyltransferase, Dol-P-Man synthase, OCh1, and Pmt1. Xylosyltransferases include, for example, protein xylosyltransferase (EC 2.4.2.26).

Presently preferred inhibitors act on enzymes selected from FTIII, FTVII, α(1,3) galactosyltransferase, ST6Gal I, ST3Gal I, GlcNAc transferase, α(1,3)Gal transferase, and UDPMurNAc transferase, UDPGlcNAc: MurNAc transferase.

Glycosyltransferase Inhibitors of the Invention

As noted above, the present invention provides methods of inhibiting glycosyltransferases. The methods comprise contacting a glycosyltransferase with an inhibitor that mimics a hydrophobic structural motif of a sugar recognized by the glycosyltransferase (e.g., in an acceptor or donor substrate), thereby inhibiting the glycosyltransferase. In a preferred aspect, the inhibitor is a non-carbohydrate hydrophobic compound that interacts with the hydrophobic amino acid residues of the active site of the glycosyltransferase.

The inhibitors usually comprise a carbocyclic (either aliphatic or aromatic) ring structure. Typically, the inhibitors comprise an aryl or a heteroaryl moiety that mimics the hydrophobic structure or face of the sugar. The aryl or heteroaryl moiety can mimic the hydrophobic structure of the acceptor substrate or the donor substrate. Typically, the rings of the inhibitors will be similar in size to the ring structure of the sugar substrate. In certain embodiments, the inhibitors of the present invention comprise a heteroaryl group including, but not limited to, quinolines, phenyl sulfonamides, phenothiazines, carbazoles, benzamides and benzopyranones, or derivatives thereof. Further preferred heteroaryl moieties include carbazoles and phenothiazines or derivatives thereof. Other inhibitors of the present invention comprise heteroaryl moieties such as thiophene, pyridines, isoxazoles, phthalimides, pyrazoles, indoles and furans or derivatives thereof.

Presently preferred inhibitors from the carbazole compound class include compounds having the structure according to Formula (I):

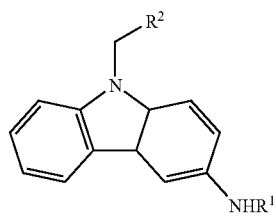

(I)

wherein,
$R^1$ is a member selected from substituted-alkyl, acylalkyl, acyl substituted-alkyl, acylheteroaryl, acyl substituted-heteroaryl, acylheterocyclyl, acyl substituted-heterocyclyl, acylaminoacyl and acyl substituted-amino acyl groups; and
$R^2$ is a member selected from H, $C_1$-$C_6$ alkyl and $C_1$-$C_6$ substituted alkyl.

In another preferred embodiment, the compounds of the invention have a structure according to Formula I, wherein
$R^1$ is a member selected from acylpyridyl, acyl substituted-pyridyl, acyl substituted-amino acyl groups, wherein the amino nitrogen of said acyl substituted-amino acyl group is substituted with a group selected from aryl and substituted aryl groups, substituted-alkyl groups, wherein said substituted alkyl group is substituted with a member selected from oxyaryl, oxy substituted-aryl, amino and alkylamino groups; and
$R^2$ is a member selected from H, $C_1$-$C_6$ alkyl and $C_1$-$C_6$ substituted alkyl.

In a still further preferred embodiment, the invention provides inhibitors having a structure according to Formula I wherein $R^1$ is a substituted alkyl group having a structure according to Formula (II):

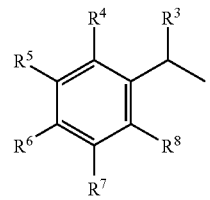

(II)

wherein,
$R^3$ is selected from alkyl and substituted alkyl;
$R^4$, $R^5$, $R^6$, $R^7$ and $R^8$ are members independently selected from H, alkyl, substituted alkyl and alkoxy groups; and
$R^2$ is a member selected from H, $C_1$-$C_6$ alkyl and $C_1$-$C_6$ substituted alkyl.

In another preferred embodiment, the invention provides inhibitors having a structure selected from the group of compounds displayed in FIG. 5.

In a further preferred embodiment, the inhibitors of the invention are selected from phenothiazine and phenothiazine substituted at one or both of the phenyl rings. Preferred substituents on the phenyl group include halogen, haloalkyl and thioalkyl groups. In a further preferred embodiment, the substituents on the phenyl group are selected from trifluoromethyl, thiomethyl and chloro groups.

In additional preferred embodiments, the thiazine-based compounds of the invention are also substituted at the thiazine nitrogen with $C_1$-$C_6$ alkyl and $C_1$-$C_6$ alkyl substituted with a group selected from heterocycles, substituted heterocycles and $NR^3R^4$, wherein $R^3$ and $R^4$ are independently H, and $C_1$-$C_6$ alkyl.

In another embodiment, wherein the thiazine nitrogen is substituted with a heterocycle, presently preferred heterocycles are selected from piperazine, N-substituted piperazine, piperidine and N-substituted piperidine.

In a further preferred embodiment, the heterocycle is selected from piperazine and piperidine moieties which are N-substituted with $C_1$-$C_6$ alkyl.

A number of heteroaryl derivatives are known to those of skill. These groups include, for example, 2-azanaphthalenyl, bezoxazolyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, thiobenzoxazolyl, thiobenzothiazolyl and thiobenzimidazolyl derivatives. The heteroaryl group can be covalently attached to other functional groups to generate a hydrophobic structural motif that mimics the acceptor substrate.

It will be apparent to those of skill in the art that in certain aspects, the heteroaryl derivatives of the present invention can be prepared using complementary functional groups. The reaction of these two functional groups, one on the heteroaryl group and the other on the derivative will provide the desired linkage. For example, the heteroaryl group may have an amine functional group, and the functional group on the derivative may be an activated carboxyl group, such as an acyl chloride or NHS ester. Reacting the two complementary functional groups together will form an amide bond between the heteroaryl group and the derivative. By suitable choice of reactive groups, the desired coupling of the heteroaryl derivative can be obtained.

In certain aspects, inhibitors of the present invention are selected by their log P value. The octanol-water partition coefficient for inhibitors can be empirically determined or can be predicted using software programs well known by those in skill in the art. In one aspect, software available from Advance Chemistry Development (ACD) is used. For instance, the ACD program calculates an accurate Log P (octanol/water partition coefficient) within ±0.3 Log P units (see, www.acdlabs.com). In one preferred aspect, the log P of the natural acceptor substrate of the glycosyl transferase and inhibitor compound are within about 3 units of each other and preferably with about 1 unit to about 2 units of each other.

In general, enzyme inhibition generally involves the interaction of a substance with an enzyme so as to decrease the rate of the reaction catalyzed by that enzyme. Inhibitors can be classified according a number of criteria. For example, they may be reversible or irreversible. An irreversible inhibitor dissociates very slowly, if at all, from its target enzyme because it becomes very tightly bound to the enzyme, either covalently or noncovalently. Reversible inhibition, in contrast, involves an enzyme-inhibitor complex that may dissociate.

Inhibitors can also be classified according to whether they are competitive, noncompetitive or uncompetitive inhibitors. In competitive inhibition for kinetically simple systems involving a single substrate, the enzyme can bind either the substrate or the inhibitor, but not both. Typically, competitive inhibitors resemble the substrate or the product(s) and bind the active site of the enzyme, thus blocking the substrate from binding the active site. A competitive inhibitor diminishes the rate of catalysis by effectively reducing the affinity of the substrate for the enzyme. Typically, an enzyme may be competitively inhibited by its own product because of equilibrium considerations. Since the enzyme is a catalyst, it is in principle capable of accelerating a reaction in the forward or reverse direction. In a presently preferred embodiment, the enzyme inhibitors of the invention are competitive with the acceptor substrate.

Noncompetitive inhibitors allow the enzyme to bind the substrate at the same time it binds the inhibitor. A noncompetitive inhibitor acts by decreasing the turnover number of an enzyme rather than diminishing the proportion of free enzyme. Another possible category of inhibition is mixed or uncompetitive inhibition, in which the inhibitor affects the binding site and also alters the turnover number of the enzyme. Enzyme inhibition of kinetically complex systems involving more than one substrate, as is the case for glycosyltransferases, are described in Segel, *Enzyme Kinetics*, (Wiley, N.Y. 1975).

Assays

After compounds are synthesized or identified, they are tested in standard assays to determine the degree to which each compound inhibits the activity of the target glycosyltransferase. Glycosyltransferase activity and its inhibition is typically assayed according to standard methods for determining enzyme activity. For a general discussion of enzyme assays, see, Rossomando, "Measurement of Enzyme Activity" in *Guide to Protein Purification*, Vol. 182, Methods in Enzymology (Deutscher ed., 1990), and Fersht, *Enzyme Structure and Mechanism* (2d ed. 1985).

An assay for glycosyltransferase activity typically contains a buffered solution adjusted to physiological pH, a source of divalent cations, a donor substrate an acceptor substrate, glycosyltransferase, and the test compound. After a predetermined time at 23° C. or 37° C., the reaction is stopped and the product is isolated and quantitated according to standard methods. For example, glycosyltransferase assays which use a UV-labeled acceptor lead to a UV-labeled product that can be readily separated by reverse phase HPLC and quantitated by UV spectroscopy are described in Schaub et al. (1998) *Glycoconjugate J.* 15: 345-354. See also, Kajihara et al., *Carbohydr. Res.* 264: C1-C5 (1994); *J. Org. Chem.* 60: 5732-5735 (1995).

To aid in the efficient identification of test compounds with inhibitory activity, assay formats that allow rapid analysis of large numbers of test compounds are preferred. For example, high throughput assays based on the ELISA format can be used (FIG. 2). In these assays one of the components of the assay (usually the acceptor sugar) is immobilized on a solid surface (e.g., the well of a microtiter plate). For example, a glycoprotein comprising the acceptor sugar can be conveniently used. The other components are added and the mixture is incubated under conditions suitable for the synthesis of the final product. An labeled antibody specifically reactive with the product is used to detect the presence of the final product. Standard means for quantifying the signal produced by the labeled antibody can be used.

Alternatively, radioactive column assays can be conveniently used (FIG. 3). In these methods either the donor or acceptor sugar is radioactively labeled (e.g., using $^{14}C$ or $^{3}H$). The other components are added and incubated under appropriate conditions. The product is then isolated from the unreacted sugars using column chromatography (e.g., separated by size or charge). The radioactivity of the fractions containing the product is measured to determine the amount of product produced.

In some embodiments, cell-based assays are used (FIG. 4). In these assays, a cell which does not naturally make the final product is transfected with nucleic acids encoding the desired glycosyltransferase. The remaining components not provided by the cell are added and the ability of the cell to make the product is detected, typically using a labeled antibody. Means for recombinantly expressing desired glycosyltransferases and detecting the presence of new carbohydrates on the surface of the cell are known (see, U.S. Pat. Nos. 5,324,663 and 5,595,900).

Test compounds that show good inhibitory properties can be further tested for their ability to inhibit various responses (e.g., immune or inflammatory) in in vitro cellular assays or in laboratory animals. Assays that are suitable for testing the effect of a glycosyltransferase inhibitor on other types of immune responses include, for example, B cell proliferation assays, CTL activation assays, and the like. Such assays are described in, for example, Hennet et al. *Proc. Nat'l. Acad. Sci. USA* 95: 4504-4509 (1998). In addition, other studies, such as those designed to analyze the time course of drugs in the body with reference to their absorption, distribution metabolism, and elimination (ADME) can carried out. Various protocols for such studies are well known.

Uses for Glycosyltransferase Inhibitors

The invention also provides methods of inhibiting glycosyltransferase-catalyzed synthesis of a particular glycoside by contacting a glycosyltransferase with a compound of the invention. The methods can be used to modulate the activity of glycosyltransferases in a number of contexts. The inhibitors of the invention can be used, for example, to control glycosyltransferase activity in vitro. For example, the inhibitors can used to inhibit glycosyltransferase activity in cell cultures used to prepare desired carbohydrate structures. The inhibitors are also conveniently used to produce animal models of disease by selectively inhibiting desired glycosyltransferases in vivo.

A number of biological processes depend upon the presence or absence of a particular carbohydrate structure. For example, the compounds can be used as antibiotics to inhibit glycosyltransferase activity in disease organisms such as bacteria, fungi and yeast. Glycosyltransferases have been implicated in a number of diseases in humans. Many disease states (e.g., inflammatory or immune responses) involve intercellular recognition mediated by cell surface receptors that include a particular oligosaccharide. For example, the ST6Gal sialyltransferase controls production of a N-linked sialoside, which is the ligand for the lectin CD22. Studies using transgenic mice in which the gene encoding the ST6Gal sialyltransferase has been knocked out suggest that the activity of this enzyme and corresponding production of the oligosaccharide are essential in promoting B lymphocyte activation and immune function (Hennet et al. *Proc Natl Acad Sci USA* 95(8):4504-9 (1998)). Other glycosyltransferases such as , FTIII, FTVII, α(1,3) galactosyltransferase, ST6Gal I, ST3Gal I, GlcNAc transferase, UDPMurNAc transferase, UDPGlcNAc: MurNAc transferase have similarly been implicated in disease processes.

Similarly, various and specific biological roles of fucosylated glycans have been reported. For example, the carbohydrate ligands for the lectin molecules termed selectins are fucosylated (Etzioni, A. et al. *Immunodeficiency* 4, 307-308 (1993)). The selectins are encoded by three genes that produce either E- L- or P-selectin. They were initially defined regarding their preferential expression on endothelium (E-selectin), leukocytes (L-selectin), and platelets (P-selectin). The selectins bind to specific glycans termed sialyl Lewis X presented on glycoproteins and perhaps glycolipids of specific cell and tissue surfaces. This structure requires both fucose and sialic acid at the outer terminus in specific linkage pattern. In addition, epithelial and gastrointestinal expression of fucose is linked to certain disease and pathogen susceptibilities, in some cases in the context of the ABO blood grouping. There is a small but significant increase in susceptibility to stomach cancer among blood type A individuals, and those with blood type O have a slightly higher incidence of peptic ulcer. Both of these disorders have been linked to an infection involving the spirochete *Helicobacter pylori*.

Fucosyltransferase activity in the stomach epithelium has been shown capable of providing an adhesion function to *Helicobacter pylori*. Fucosylation of the gastric epithelium can therefore modulate the adhesion and colonization of this pathogenic organism in humans. *H. pylori* colonizes the stomach of at least half of all humans surveyed. A subpopulation of humans infected with *H. pylori* go on to develop gastric and duodenal ulcers. How the bacterium attaches to host cells has been the subject of intense investigation. Among the candidate adhesion receptors that appear associated with gut inflammatory disease is the fucosylated carbohydrate, Lewis b (Ilver et al. *Science* 279:373-377 (1998). Lewis b (Fucα1,2Galβ1,3(Fucα1,4)GlcNAc-R) is the product of two fucosyltransferases, FucT-II and FucT-III. (Falk et al. *Proc Natl Acad Sci USA* 92, 1515-1519 (1995) and Guruge et al. *Proc Natl Acad Sci USA* 95,3925-3930 (1998)).

In addition, specific carbohydrates have been implicated in angiogenesis (WO98/48817). Thus, control of the synthesis of these structures can be used to treat angiogenesis associated with cancer and other diseases. Similarly, inhibitors of glycosyltransferases can be used as antibacterial compounds. For example, known antibacterial compounds, such as ramoplanin and vancomycin are known to inhibit enzymes involved in carbohydrate synthesis. Thus, the compounds of the invention can be used as therapeutic compounds for treatment of human diseases, antibiotics, insecticides, and the like. In one preferred embodiment, the compounds of the invention are used for therapeutic treatment of disease.

The compositions and methods of the present invention find use in both therapeutic and diagnostic applications. For instance, the glycosyltransferase inhibitors, which can act as substrate analogs, are used for in vitro diagnosis of cells, (e.g., cancer cells) that express the particular glycosyltransferase of interest. Moreover, inhibitors of α(1,3) galactosyl transferases can be used to retard or prevent the rejection of xenografts. The response of the cells to a biologically effective dose of the agent can then be determined.

The glycosyltransferase inhibitor compounds of the invention also find use therapeutically to selectively inhibit glycosyltransferase activity associated with a variety of immune responses. For example, the inhibitors of the invention can be used to inhibit deleterious immune responses associated with autoimmune disease, graft rejection and allergies. Inappropriate activation of the immune system is a component of a number of immunopathologies, such as autoimmunity, allograft rejection and allergic responses. Exemplary autoimmune diseases include rheumatoid arthritis, multiple sclerosis, lupus, scleroderma and myasthenia gravis. Allergic responses include allergies to various pollens, dust mites and the like. In addition, foreign infectious diseases may cause immunopathology (e.g., lyme disease, hepatitis, LCMV, post-streptococcal endocarditis, or glomerulonephritis). Food hypersensitivities, such as celiac disease and Crohn's disease, as well as other allergic diseases, have been associated with inappropriate immune responses or suspected of having an autoimmune component.

Other disorders treatable by compositions of the present invention include, e.g., rheumatoid arthritis, post-ischemic leukocyte-mediated tissue damage (reperfusion injury), acute leukocyte-mediated lung injury (e.g., adult respiratory distress syndrome), septic shock, and acute and chronic inflammation, including atopic dermatitis and psoriasis. In the case of reperfusion injury, the blocking agents are ideally used prophylactically prior to heart surgery to enhance post-surgical recovery. In addition, tumor metastasis can be prevented by inhibiting the adhesion of circulating cancer cells. Examples include carcinoma of the colon and melanoma.

In therapeutic applications, the glycosyltransferase inhibitors of the invention are administered to an individual already suffering from an inappropriate or undesirable immune response. Compositions that contain the glycosyltransferase inhibitors are administered to a patient in an amount sufficient to suppress the undesirable immune response and to cure or at least partially arrest symptoms and/or complications. An amount adequate to accomplish this is defined as a "therapeutically effective dose." Amounts effective for this use will depend on, e.g., the inhibitor composition, the manner of administration, the stage and severity of the disease being treated, the weight and general state of health of the patient, and the judgment of the prescribing physician.

It must be kept in mind that the compositions of the present invention may be employed in serious disease states, that is, life-threatening or potentially life threatening situations. In such cases, in view of the minimization of extraneous substances and the relative nontoxic nature of the inhibitors, it is possible and may be felt desirable by the treating physician to administer substantial excesses of these compositions.

The dose of the glycosyltransferase inhibitor of the invention for treatment of inflammatory disease will vary according to, e.g., the particular inhibitor, the manner of administration, the particular disease being treated and its severity, the overall health and condition of the patient, and the judgment of the prescribing physician.

The pharmaceutical compositions are intended for parenteral, topical, oral or local administration, such as by aerosol or transdermally, for prophylactic and/or therapeutic treatment. For topical application, non-sprayable forms, viscous to semi-solid or solid forms comprising a carrier compatible with topical application and having a dynamic viscosity preferably greater than water are typically used. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc.

For aerosol administration, the compounds are preferably supplied in finely divided form along with a surfactant and propellant. Typical percentages of blocking agents are 0.1%-10% by weight, preferably 1%-5%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arbitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%-20% by weight of the composition, preferably 0.25-5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

This invention also provides compositions for intravenous administration which comprise a solution of the glycosyltransferase inhibitor dissolved or suspended in an acceptable carrier, preferably an aqueous carrier. A variety of aqueous carriers may be used, e.g., water, buffered water, 0.4% saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the glycosyltransferase inhibitor that can be combined to form a "cocktail" under certain circumstances for increased efficacy in the pharmaceutical formulations can vary widely, i.e., from less than about 0.05%, usually at or at least about 1% to as much as 10 to 30% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and a unit dosage comprising 2-2,000 mg of the compound. Actual methods for preparing parenterally administrable compounds will be known or apparent to those skilled in the art and are described in more detail in for example, *Remingtons Pharmaceutical Sciences*, 18th ed., Mack Publishing Company, Easton, Pa. (1990). For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more glycosyltransferase inhibitors of the invention, preferably 15%.

The glycosyltransferase inhibitors of the invention can also be administered via liposomes, which serve to target the conjugates to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide or conjugate of the invention can be directed to the site of lymphoid cells, where the liposomes then deliver the selected glycosyltransferase inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., *Ann. Rev. Biophys. Bioeng.* 9:467 (1980); U.S. Pat. Nos. 4,235,871, 4,501,728 and 4,837,028.

The targeting of liposomes using a variety of targeting agents is well known in the art (see, e.g., U.S. Pat. Nos. 4,957,773 and 4,603,044). For targeting to the immune cells, a ligand to be incorporated into the liposome can include, e.g., antibodies or fragments thereof specific for cell surface determinants of the desired immune system cells. A liposome suspension containing a peptide or conjugate may be administered intravenously, locally, topically, etc. in a dose which varies according to, inter alia, the manner of administration, the conjugate being delivered, and the stage of the disease being treated.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective dose." Unit dosages effective for this use will depend on the severity of the disease and the weight and general state of the patient, but generally range from about 0.5 mg to about 10 g of glycosyltransferase inhibitor for a 70 kg patient, usually from about 10 mg to about 5 g, and preferably between about 2 mg and about 1 g. Therapeutic administration may begin at the first sign of disease or the detection or shortly after diagnosis in the case of immune disorder. This is often followed by repeated administration until at least symptoms are substantially abated and for a period thereafter. These doses can be followed by repeated administrations over weeks to months depending upon the patient's response and condition.

In prophylactic applications, compositions containing the compounds of the invention are administered to a patient susceptible to or otherwise at risk of a particular disease. Such an amount is defined to be a "prophylactically effective dose." For prophylactic use, the inhibitor compounds are administered to risk groups. In this use, the precise amounts again depend on the patient's state of health and weight, but generally range from about 0.5 mg to about 10 g of glycosyltransferase inhibitor for a 70 kg patient, usually from about 10 mg to about 5 g, and preferably between about 2 mg and about 1 g.

Single or multiple administrations of the compositions can be carried out with dose levels and pattern being selected by the treating physician. In any event, the pharmaceutical formulations should provide a quantity of inhibitor of this invention sufficient to effectively treat the patient.

The effect of administration of the glycosyltransferase inhibitors of the invention can be monitored by detecting the levels of product glycosides in a sample from a patient. This can be performed according to standard methods for detection of desired carbohydrate structures. For instance, specific lectins or antibodies raised against the ligand can be used. Particular lectins are well known and commercially available (e.g., from Sigma Chemical Co., St. Louis Mo.).

Glycosyltransferases themselves, in particular the acceptor binding domain of a glycosyltransferase, are also useful as binding moieties in the diagnostic assays of the invention. In the absence of a particular glycosyltransferase, for example, the concentration of acceptor moieties tends to increase. As an example, a deficiency of ST6Gal sialyltransferase causes a dramatic increase in terminal galactose residues (i.e., Galβ1,4GlcNAc-) on B cells. Thus, one can use the ST6Gal sialyltransferase as a detection moiety to determine whether ST6Gal is deficient in the cells. An ST3Gal transferase can be used similarly as a detection moiety.

In typical embodiments, the detection moieties are labeled with a detectable label. The detectable labels can be primary labels (where the label comprises an element that is detected directly or that produces a directly detectable element) or secondary labels (where the detected label binds to a primary label, as is common in immunological labeling). An introduction to labels, labeling procedures and detection of labels is found in Polak and Van Noorden (1997) *Introduction to Immunocytochemistry*, 2nd ed., Springer Verlag, N.Y. and in Haugland (1996) *Handbook of Fluorescent Probes and Research Chemicals*, a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

Preferred enzymes that can be conjugated to detection reagents of the invention include, e.g., luciferase, and horse radish peroxidase. The chemiluminescent substrate for luciferase is luciferin. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art.

In general, a detector which monitors a particular label is used to detect the label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Efficacy of a treatment regime is indicated by a substantial reduction of product glycosides in a sample obtained from the patient. Alternatively, methods for detecting levels of specific glycosyltransferase activities can be used. Standard assays for detecting glycosyltransferases such as the ST6Gal and ST3Gal I are known to those of skill in the art. Again, treatment efficacy is indicated by a substantial reduction in activity of the particular glycosyltransferase. As used herein, a "substantial reduction" in the appropriate sialylgalactoside levels or glycosyltransferase activity refers to a reduction of at least about 30% in the test sample compared to a non-immunodeficient control. Preferably, the reduction will be at least about 50%, more preferably at least about 75%, and most preferably sialylgalactoside or glycosyltransferase levels will be reduced by at least about 90% in a sample from a treated mammal compared to an untreated control.

EXAMPLES

The following example provides exemplary assay protocols of the invention.

FTVII Assay Protocol

Fluoronunc Maxisorp Microtiterplate plates (Nunc Cat# 437958) were coated with 100 µl/well of the acceptor substrate, Sialyl-LNnt BSA(10 µg/ml in PBS), either overnight at 4° C. or for 2 hours at 37° C. The plates were then washed with 100 µl/well of PBS, and then blocked with Superblock (Pierce Cat# 37535) (200 µl/well) for 1 hour at room temperature. The plates were then washed with 200 µl/well of TBS/Tween (Tris-Buffered Saline+Tween: 25 mM Tris, 0.1M NaCl, 0.02% Tween 20, 0.02% sodium azide, pH 7.5)

| The assay mix comprised: | TBS: Tween | |
|---|---|---|
| | GDP fucose | 100 µM |
| | $MnCl_2$ | 10 µM |
| | FTVII enzyme | 6.2 mUnits/ml |

The assay mix (100 µl/well) was added and the plates were incubated for 90 minutes at 37° C. After the incubation period, the plates were washed twice with TBS:Tween and once with TBS-10B (TBS diluted 10-fold with H20 plus 0.25% BSA, 0.02% Tween 20). An antibody specific to the product (the CSLEX antibody) was then added at 1:30 dilution in TBS-10B and incubated for 1 hour at room temperature. The plates were then washed again three times with TTBS-10B, 200 µl/well. The peroxidase conjugated anti-murine IgM diluted 1 to 1000 in TTBS-10B was added to the plates (100 µl/well) and the plates were incubated for 1 hour at room temperature. The plates were then washed six times with TTBS-10B (100 µl/well). The TMB substrate (100 µl/well) was added to the plates and the color was allowed to develop for 15 minutes at room temperature. Phosphoric acid (1M) was added to the plates (100 µl/well), to stop the peroxidase reaction and after mixing the absorbance was read at 450 nm.

ST6 GAL 1 Assay Protocol

Immulon4 ELISA plates (96 well, Dynex (Cat #G2402-958) were coated with the acceptor substrate asialo-fetuin in PBS (150 mM NaCl, 6.7 mM $KH_2PO_4$, 0.02% $NaN_3$, pH7.4) at a concentration of 20 µg/ml (100 µl/well) and the acceptor was allowed to adhere to the plate overnight at 4° C. The coating solution was removed by aspirating and the wells were washed with 3×200 µl of PBS. The wells were then blocked with PBS plus 1% gelatin, 200 µl/well for 45-60 minutes at room temperature. After washing the wells three times with PBS, 100 µl of the assay mix containing 250 µUnits/ml of human ST6Gal I in reaction buffer (50 mM MES, pH6.0, 100 µM CMP-Neu5Ac) was added to the wells and allowed to incubate at 37° C. for 45 minutes. Enzyme incubation was terminated by the aspiration of well contents. The wells were then washed with 3×200 µl of PBS containing 0.05% Tween 20 (PBST). The α2,6 sialylated product was detected by Emporium-labeled *Sambucus nigra* agglutinin (SNA). The wells were overlaid with 100 µl of SNA in PBST at 1 µg/ml for 45 minutes at room temperature, followed by 4×100 µl washes with PBST. Europium enhancing reagent (naphthoyltrifluoroacetone+0.1% Triton X-100) was added at 50 µl/well and after a 30 minute incubation at room temperature, the plates were read on a BMG Fluostar plate reader with excitation at 340±35 nm and emission at 615±10 nm. To ensure that the detection reagent is effective, fetuin at 20 µg/ml is used as a control.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of identifying an inhibitor of a glycosyltransferase that transfers a monosaccharide from a sugar nucleotide to an acceptor sugar, wherein the glycosyltransferase comprises an active site comprising hydrophobic amino acids that interact with a sugar substrate, the method comprising
   contacting the glycosyltransferase, an acceptor sugar, and a sugar nucleotide with a hydrophobic, non-carbohydrate test compound suspected of inhibiting interaction of a sugar with hydrophobic amino acids in the active site of the glycosyltransferase and
   determining the degree to which the activity of the glycosyltransferase is inhibited in the presence of the test compound.

2. The method of claim 1, wherein the activity of the glycosyltransferase is determined using an antibody that is specifically immunoreactive with a product of the reaction catalyzed by the glycosyltransferase.

3. The method of claim 2, which is an ELISA format.

4. The method of claim 1, wherein the glycosyltransferase is expressed in a recombinant cell.

5. The method of claim 1, wherein the sugar nucleotide or acceptor sugar is labeled.

6. The method of claim 5, wherein the label is a fluorescent label.

7. The method of claim 1, wherein the glycosyltransferase is a fucosyltransferase.

8. The method claim 1, wherein the compound comprises a heteroaryl moiety.

9. The method of claim 8, wherein the heteroaryl moiety is selected from the group consisting of a thiophene, pyridine, isoxazole, phthalimide, pyrazole, indole, quinoline, phenothiazine, carbazole, benzopyranone, and a furan group.

10. The method of claim 1, wherein the hydrophobic, non-carbohydrate test compound comprises a member selected from the group consisting of a heteroaryl moiety having from 5 to 16 ring members wherein from 1 to 3 ring members are each independently selected from the group consisting of N, O and S wherein the heteroaryl ring structure is optionally substituted, and an aliphatic ring structure having from 3 to 7 ring members and is optionally substituted.

* * * * *